United States Patent
Krivitski (10) Patent No.: US 8,162,843 B2
(45) Date of Patent: Apr. 24, 2012

(54) METHOD FOR MEASURING CARDIAC OUTPUT VIA AN EXTRACORPOREAL CARDIOPULMONARY SUPPORT CIRCUIT

(75) Inventor: Nikolai M. Krivitski, Ithaca, NY (US)

(73) Assignee: Transonic Systems, Inc., Ithaca, NY (US)

( * ) Notice: Subject to any disclaimer, the term of this patent is extended or adjusted under 35 U.S.C. 154(b) by 859 days.

(21) Appl. No.: 11/781,536

(22) Filed: Jul. 23, 2007

(65) Prior Publication Data

US 2008/0033314 A1 Feb. 7, 2008

Related U.S. Application Data

(63) Continuation of application No. 10/937,191, filed on Sep. 9, 2004, now Pat. No. 7,261,696.

(51) Int. Cl.
*A61B 5/0275* (2006.01)
*A61B 5/02* (2006.01)
(52) U.S. Cl. .......... 600/526; 600/508; 600/481
(58) Field of Classification Search .......... 600/481–528
See application file for complete search history.

(56) References Cited

U.S. PATENT DOCUMENTS

| | | | |
|---|---|---|---|
| 4,015,593 A * | 4/1977 | Elings et al. | 600/526 |
| 4,995,268 A * | 2/1991 | Ash et al. | 73/861.05 |
| 5,685,989 A | 11/1997 | Krivitski et al. | |
| 5,928,180 A | 7/1999 | Krivitski et al. | |
| 6,061,590 A | 5/2000 | Krivitski | |
| 6,155,984 A | 12/2000 | Krivitski | |
| 6,308,737 B1 * | 10/2001 | Krivitski | 137/597 |
| 6,493,567 B1 | 12/2002 | Krivitski et al. | |
| 6,548,017 B2 | 4/2003 | Krivitski et al. | |
| 6,585,675 B1 * | 7/2003 | O'Mahony et al. | 604/4.01 |
| 6,695,807 B2 * | 2/2004 | Bell et al. | 604/6.16 |
| 6,718,190 B2 | 4/2004 | Krivitski et al. | |
| 6,726,647 B1 | 4/2004 | Sternby et al. | |
| 6,752,771 B2 | 6/2004 | Rothman et al. | |
| 6,757,554 B2 | 6/2004 | Rubinstein et al. | |
| 6,758,822 B2 | 7/2004 | Romano | |
| 6,761,700 B2 | 7/2004 | Sirimanne et al. | |
| 7,172,570 B2 * | 2/2007 | Cavalcanti et al. | 604/6.11 |
| 7,384,543 B2 * | 6/2008 | Jonsson et al. | 210/97 |
| 2004/0158133 A1 * | 8/2004 | Krivitski et al. | 600/322 |

* cited by examiner

*Primary Examiner* — Charles A Marmor, II
*Assistant Examiner* — Karen Toth
(74) *Attorney, Agent, or Firm* — Brian B. Shaw, Esq.; Harter Secrest & Emery LLP (57) ABSTRACT

A method for determining cardiac output in conjunction with flow through an extracorporeal circuit, wherein flow through an arterial line of the extracorporeal circuit is temporarily reversed and an indicator is passed through the cardiopulmonary circuit. A dilution curve is measured in the arterial line of the extracorporeal circuit during the reversed flow, and cardiac output is determined corresponding to the measured dilution curve.

20 Claims, 7 Drawing Sheets

METHOD FOR MEASURING CARDIAC OUTPUT VIA AN EXTRACORPOREAL CARDIOPULMONARY SUPPORT CIRCUIT

CROSS-REFERENCE TO RELATED APPLICATIONS

The present application is a continuation of U.S. application Ser. No. 10/937,191 filed Sep. 9, 2004, hereby expressly incorporated by reference.

STATEMENT REGARDING FEDERALLY SPONSORED RESEARCH OR DEVELOPMENT

Not applicable.

REFERENCE TO A "SEQUENCE LISTING"

Not applicable.

BACKGROUND OF THE INVENTION

1. Field of the Invention

The present invention relates to determining cardiac output of a patient, and more particularly, to determining the cardiac output of a patient through an extracorporeal cardiopulmonary support circuit, wherein flow through at least a portion of the extracorporeal cardiopulmonary support circuit is reversed and a measurement at the reversed flow is taken from which the cardiac output is determined.

2. Description of Related Art

Respiratory failure requiring pulmonary support affects in excess of 300,000 people in the United States per year. Approximately one-half of these patients suffer from adult respiratory distress syndrome (ARDS). Adult respiratory distress syndrome is an acute inflammatory lung disease with a mortality rate of 50%. This disease is characterized by increased capillary permeability resulting from the development of interstitial edema and alveolar flooding. For the vast majority of patients with ARDS, there is no specific treatment, or supportive therapy. Supportive therapy for ARDS focuses on mechanical ventilation. An alternative life support modality, such as extracorporeal oxygenation, can be a therapeutic option for acute respiratory failure in both infants and adults.

In addition, extracorporeal circulation (perfusion) is used for the most part in cardiac bypass surgery. In a total bypass, all the systemic venous return blood of the patient is diverted from entering the right side of the heart and into an extracorporeal circuit. In such application, the extracorporeal circuit includes a heart-lung machine that comprises a pumping function and an oxygenation function, completely taking over cardiopulmonary function for the patient, returning oxygenated blood to the aorta, downstream of the cardiopulmonary circuit. In a partial bypass only a portion of the blood is diverted to the extracorporeal circuit, the remaining flow passing to the heart, the lungs and from the lungs through heart to the systemic circulation.

A use of extracorporeal circulation as "extracorporeal life support" can include "extracorporeal membrane oxygenation" known by the respective acronyms of "ECLS" or "ECMO", for simplicity herein called ECMO. As opposed to the more conventional extracorporeal circulation and substitution or assist of the cardiac function, ECMO connotes the application of such support to supply oxygenation where the native lungs may be compromised. This is especially useful for neonates, including premature birth babies, whose life is threatened because their immature lungs cannot provide adequate gas exchange. Another use is resuscitated drowning victims whose lungs are damaged and unable to supply adequate oxygenation without restorative healing. The extracorporeal circulation provides oxygenated blood to the lungs under the impetus of the patient's native heart and gives time to allow healing of the lungs to occur until the lungs can take over oxygenation. In excess of 1,000 ECMO procedures are conducted annually in the United States.

Another use of extracorporeal circulation is to provide heart support without supplementary oxygenation. For examples part of the blood flow bypasses the heart and instead passes through the extracorporeal circuit, thereby reducing a portion of the load on the heart.

While the applications and successes of extracorporeal circulation have been increasing, the need remains for limiting the duration of the extracorporeal circulation to a substantially as needed basis. The need exists for determining the as needed basis in terms of measuring patient performance during the extracorporeal circulation. A need exists for determining cardiac output during extracorporeal circulation. The need exist for determining cardiac output without requiring further intervention or cessation of treatment.

BRIEF SUMMARY OF THE INVENTION

One configuration provides a method and apparatus for determining cardiac output of a patient on extracorporeal circulation including, but not limited to extracorporeal life support. By monitoring the cardiac output, the extracorporeal circulation can be controlled to correspond to the capacity of the patient so as to minimize excessive extracorporeal circulation time. In addition, selected configurations can provide real time assessment of heart performance, and particularly as in response to a substantially contemporaneous or prior treatment.

The present method provides for measuring a patient cardiac output with an extracorporeal cardiopulmonary support device withdrawing blood from a venous portion of a patent vascular system through an extracorporeal venous line and delivering blood to an arterial portion of the patient vascular system through an arterial extracorporeal line, then temporarily reversing flow in the extracorporeal venous line and the extracorporeal arterial line for withdrawing the blood and a portion of the dilution indicator, measuring a dilution curve in the extracorporeal system and determining a cardiac output corresponding to the measured dilution curve. Preferably, the dilution curve is measured in the arterial line of the extracorporeal circuit.

The apparatus for determining the cardiac output includes means for reversing the flow in at least the arterial line of the extracorporeal circuit, means for introducing a dilution indicator to pass through the cardiopulmonary circuit, a sensor for measuring a dilution curve of the dilution indicator in the extracorporeal circuit, and preferably in the arterial line, and a controller for determining the cardiac output corresponding to the measured dilution curve.

DETAILED DESCRIPTION OF THE INVENTION

Figure 1:
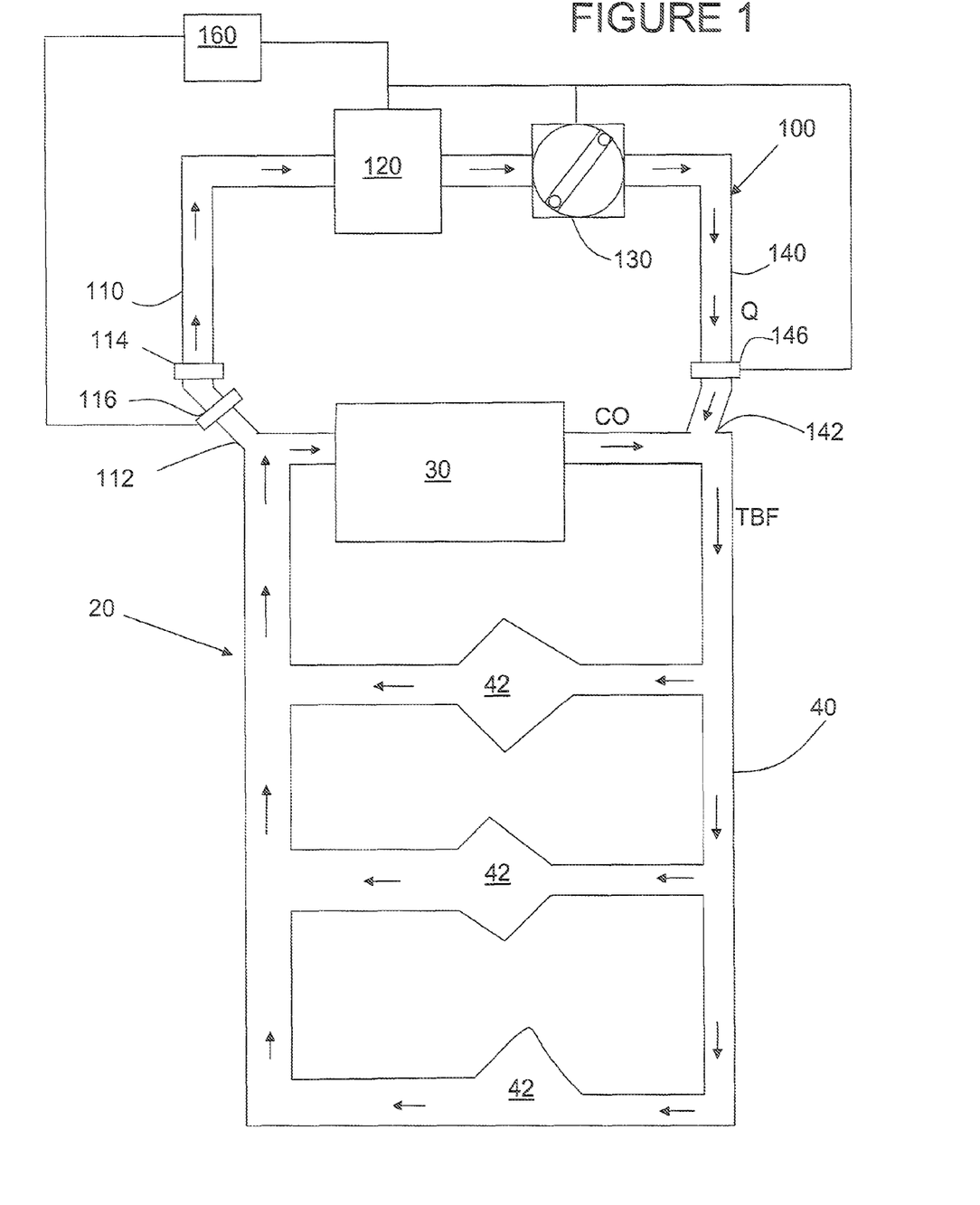
FIG. 1 is a schematic of the circulatory system showing the cardiopulmonary and systemic circuit with a connected extracorporeal circuit in a normal, or forward extracorporeal flow configuration.

Referring to FIG. 1, an extracorporeal circuit 100 is shown connected to a circulation system 20.

The circulation system 20 is a human (or animal) circulatory system including blood, a vascular system, and a heart. For purposes of this description, the circulation system 20 is represented as a cardiopulmonary system 30 and a systemic system 40 connecting the cardiopulmonary system 30 to the tissues of the body. Specifically, the systemic system 40 passes the blood though the vascular system (arteries, veins, and capillaries 42) throughout the body. The portal circulation is taken as part of the systemic system 40.

The cardiopulmonary system 30 includes the right heart, the lungs and the left heart, as well as the vascular structure connecting the right heart to the lungs, the lungs to the left heart and some portion of the aorta and large veins located between the extracorporeal circuit and the right and left heart. That is, in theory the cardiopulmonary system 30 would include only the right heart, the lungs, the left heart and the vascular structure directly connecting the right heart to the lungs and the lungs to the left heart. However, in practice it is sometimes impracticable to operably connect the extracorporeal circuit 100 immediately adjacent the large vein at the right heart, or immediately adjacent the aorta at the left heart. Therefore, the cardiopulmonary system 30 often includes a limited length of the vein entering the right heart and the aorta exiting the left heart. For example, the extracorporeal circuit 100 can be connected to a femoral artery and femoral vein, thereby effectively extending the cardiopulmonary system 30 to such femoral artery or vein.

For cardiopulmonary and vascular systems, the term "upstream" of a given position refers to a direction against the flow of blood, and the term "downstream" of a given position is the direction of blood flow away from the given position. The "arterial" side or portion is that part in which oxygenated blood flows from the heart to the capillaries. The "venous" side or portion is that part in which blood flows from the capillaries to the heart and lungs (the cardiopulmonary system 30).

The basic components of the extracorporeal circuit 100 for a conventional heart-lung machine include a venous line 110, a venous reservoir (not shown), an oxygenator 120 and heat exchanger (not shown), a pump 130, an arterial line filter (not shown), an arterial line 140, a dilution sensor 146 in the arterial line and a controller 160

Generally, the extracorporeal circuit 100 withdraws blood from the venous portion of the circulation system 20 (or cardiopulmonary system 30), and returns the blood to the arterial portion of the circulation system. The withdrawn blood can be treated while it is withdrawn, or the withdrawn blood can be merely returned to the arterial portion of the circulation system 20. The blood treatment, if applied, can be any of a variety of treatments including, but not limited to, oxygenation (and carbon dioxide withdrawal).

The venous line 110 extends from the venous portion of the circulation system 20, and preferably from a venous portion of the cardiopulmonary system 30. The venous line 110 typically includes a venous cannula 112 providing the fluid connection to the circulation system 20.

The venous line 110 can also include or provide a site 114 for introduction of the dilution indicator. In a preferred configuration, the site 114 for introducing the dilution indicator is proximal to the interface of the venous line 110 and the circulation system 20. In selected configurations, the introduction site 114 can be integrated into the venous cannula 112.

If the venous dilution senor 116 is used, then the injection site 114 should be distal to the sensor so when flow is reversed, the injected indicator first passes the sensor prior entering venous system through cannula 112.

It is also contemplated, that a component of the extracorporeal circuit 100 can be controlled to create or induce an indicator within the flow in the extracorporeal circuit. For example, a filtration or treatment rate can be sufficiently changed to create an effective indicator in the extracorporeal circuit 100 which then travels through the cardiopulmonary system 30.

In addition, the venous line 110 can include a dilution sensor 116. The dilution sensor 116 (as well as sensor 146) can be any of a variety of sensors, and can cooperate with the particular indicator. The sensor 116 (as well as sensor 146) can measure different blood properties: such as but not limited to temperature, electrical impedance, optical properties, density, ultrasound velocity, concentration of glucose and other blood substances (any physical or chemical blood properties). Preferably, the sensor 116 is close to the venous point of cannulation 112, (the interface of the venous line 110 and the circulation system 20).

The arterial line 140 connects the extracorporeal circuit 100 to an arterial portion of the circulation system 20 and preferably to an arterial portion of the cardiopulmonary system 30. The arterial line 140 usually connects to the ascending aorta. However, the arterial line 140 can be placed downstream in the arterial portion of the vascular system for example into femoral artery, or carotid artery, where the vessel is sufficiently large to accommodate the necessary flow rate. The arterial line 140 typically includes an arterial cannula 142 providing the fluid connection to the circulation system 20.

The arterial line 140 also includes the dilution sensor 146. The sensor 146 can be any of a variety of sensors, as set forth in the description of the sensor 116, and is typically selected to cooperate with the anticipated indicator. Preferably, the sensor 146 is proximal (close to) to the point of arterial cannulation, (the interface of the arterial line 140 and the circulation system 20).

However, it is understood the sensor 146 can be located anywhere in the extracorporeal circuit 100 or even outside of the extracorporeal circuit. That is, the sensor 146 can be remotely located and measure in the extracorporeal circuit 100, and preferably in the arterial line 140, the changes produced in the blood from the indicator introduction or values related to the indicator introduction which can be transmitted or transferred by means of diffusion, electro-magnetic or thermo fields or by other means to the location of the sensor.

Current oxygenators 120 are broadly classified into bubble type and oxygenators and membrane type oxygenators. The membrane type oxygenators fall under the laminate type, the coil type, and the hollow fiber type. Membrane type oxygenators offer advantages over the bubble type oxygenators as the membrane type oxygenators typically cause less blood damage, such as hemolysis, protein denaturation, and blood coagulation as compared with the bubble type oxygenators. Although the preferred configuration is set forth in terms of a membrane type oxygenator, it is understood any type of oxygenator can be employed or no oxygenator can be used in the extracorporeal circuit.

The pump 130 can be any of a variety of pumps types, including but not limited to a roller (or impeller) pump. The pump 130 induces a blood flow through the extracorporeal circuit 100. At least one of the pump 130 and the controller 160 typically include control of the rpm of the pump and the flow rate of the blood through the pump, respectively. The pump 130 can be at any of a variety of locations in the extracorporeal circuit 100, and is not limited to the position shown in the Figures.

The controller 160 is typically connectable to the oxygenator 120, the pump 130 and the sensor(s) 116, 146. The controller 160 can be a stand alone device such as a personal computer, a dedicated device or embedded in one of the components, such as the pump 130 or the oxygenator 120. Although the controller 160 is shown as connected to the sensors 116 and 146, the pump 130 and the oxygenator 120, it is understood the controller can be connected to only the sensors, the sensors and the pump, or any combination of the sensors, pump and oxygenator.

The normal or forward blood flow through the extracorporeal circuit 100 includes withdrawing blood through the venous line 110 from the venous side circulation system 20 (and particularly the cardiopulmonary circuit 30), passing the withdrawn blood through the extracorporeal circuit (to optionally treat such as oxygenate, or merely circulate the withdrawn blood), and introducing the withdrawn (or treated) blood through the arterial line 140 into the arterial side of the circulation system (and particularly the arterial portion of the cardiopulmonary circuit). The pump 130 thereby normally induces a blood flow through the extracorporeal circuit 100 from the venous line 110 to the arterial line 140.

Thus, the forward flow through the extracorporeal circuit 100 is parallel to the flow from the venous side of the circulation system 20 (through the cardiopulmonary system 30, the right heart, the lungs, a left heart) and passing to the arterial portion of the systemic system 40.

While cardiopulmonary support offers life-saving and life prolonging treatment, the intrusive nature of the cardiopulmonary support carries significant risks and potential complications. Each additional hour of unnecessary cardiopulmonary support increases the probability of negative complications as well as increasing the already substantial costs of the treatment. Therefore, it is desirable to limit the duration of cardiopulmonary support as required by the individual patient. One of the main criteria for decreasing or terminating cardiopulmonary support is an adequate increase in the heart flow-cardiac output. Typically, cardiopulmonary support can be decreased as the normal heart capacity is restored.

The heart capacity (flow) is typically measured by cardiac output CO. Cardiac output CO is the amount of blood pumped out by the left ventricles in a given period of time (typically a 1 minute interval).

Referring to FIG. 1, the total blood flow (TBF) passing to the systemic system 40 is the sum of the cardiac output CO (blood flowing from the cardiopulmonary system 30) and the blood flow Q from the extracorporeal circuit 100.

$$TBF = CO + Q \quad \text{(Eq. 1)}$$

To apply the present dilution technique to measure cardiac output CO during circulation in the extracorporeal circuit 100, the blood flow is reversed in at least the arterial line 140, and the venous line 110 if there is no buffer in the extracorporeal circuit 100. Thus, blood is withdrawn from the arterial side of the circulation system 20, passed through the extracorporeal circuit 100 and delivered to the venous side of the circulation system 20. That is, the flow in the extracorporeal circuit 100 is reversed relative to the circulation system 20. During the reversed flow in the extracorporeal circuit 100, the dilution indicator injected into the venous line (of extracorporeal circuit 100 or intravascuiar system, such as circulation system 20) will pass through any incorporated portion of the venous portion of the circulation system 20, the cardiopulmonary circuit 30 (the right heart, the lungs, the left heart) and will be sampled (dilution curve recorded or measured) in the of the extracorporeal circuit, and preferably in arterial line 140.

Figure 2:
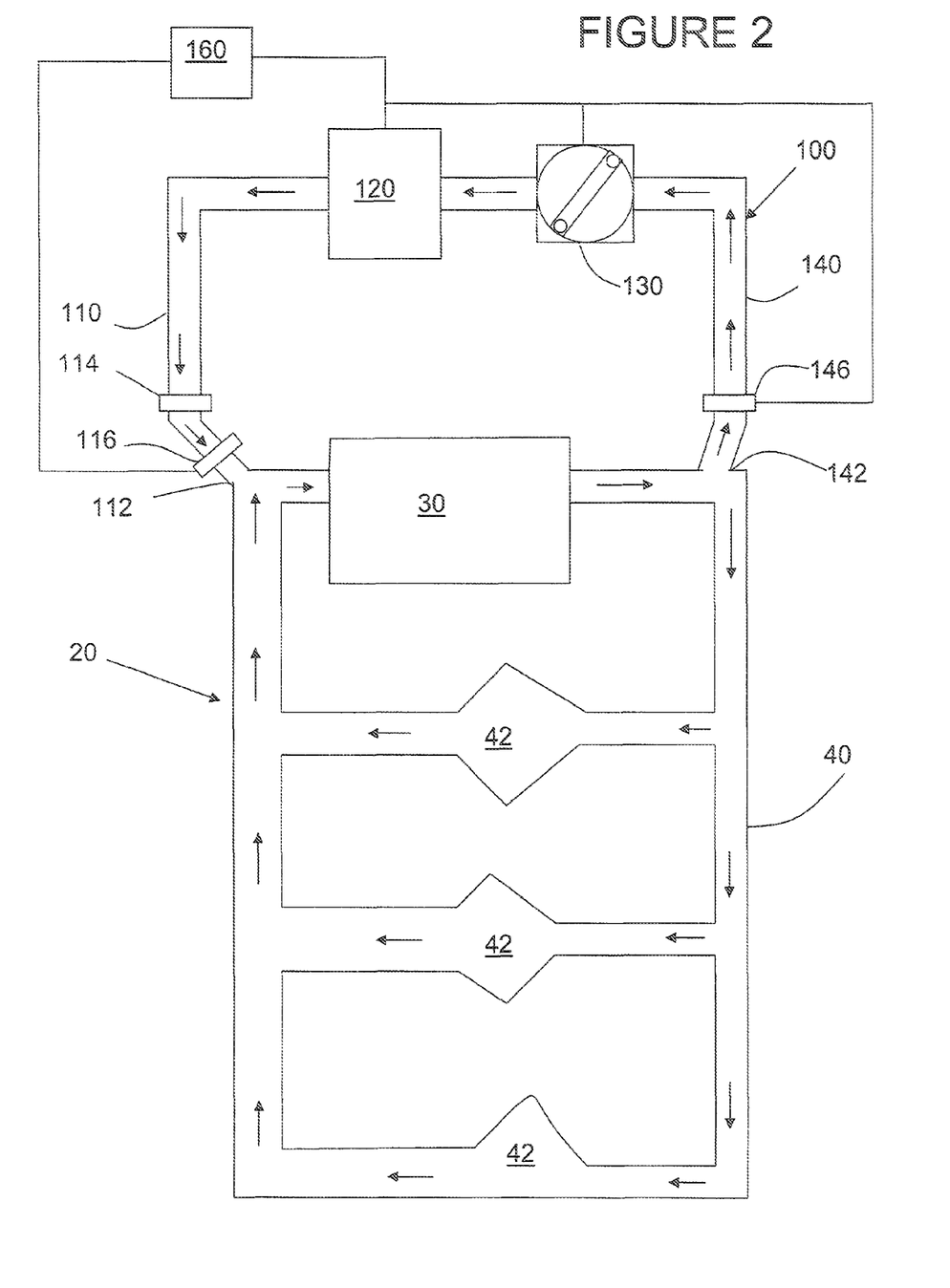
FIG. 2 is the schematic of FIG. 1 showing a reversed extracorporeal flow configuration, such as by extracorporeal pump reversal.

The flow can be reversed by a number of configurations. Referring to FIG. 2, the direction of the pump 130 can be temporarily reversed (for example, on the order of 2-5 minutes). In this case, injection of the indicator can be made anywhere into the extracorporeal circuit 100, though preferably at the site 114 in the venous line 110. The indicator will then pass through the cardiopulmonary system 30 and a portion of the indicator then passes into the arterial line 140 of the extracorporeal circuit 100. The resulting dilution curve can be measured anywhere in the extracorporeal circuit 100, and preferably in the arterial line 140. The resulting dilution curve is recorded, or measured and from which the cardiac output CO is calculated.

However, components of the extracorporeal circuit 100, such as (bubble traps, oxygenators) are typically designed to permit only single direction (normal or forward) flow. Therefore, for this configuration to be implemented, the components of the extracorporeal circuit 100 must be compatible for bidirectional flow.

Figure 3:
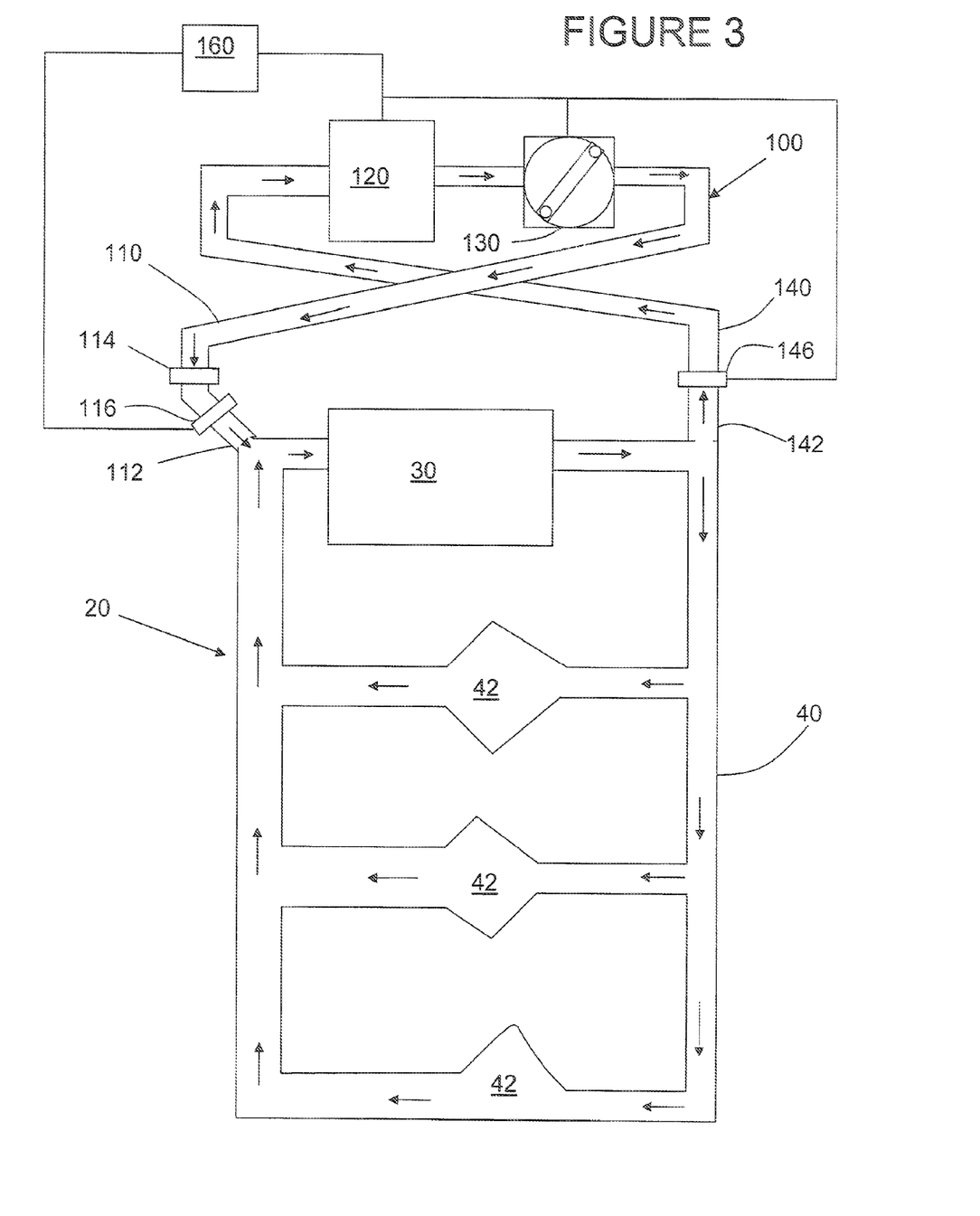
FIG. 3 is a schematic of an extracorporeal circuit with a reversed extracorporeal flow configuration, such as by extracorporeal line reversal.
Figure 5:
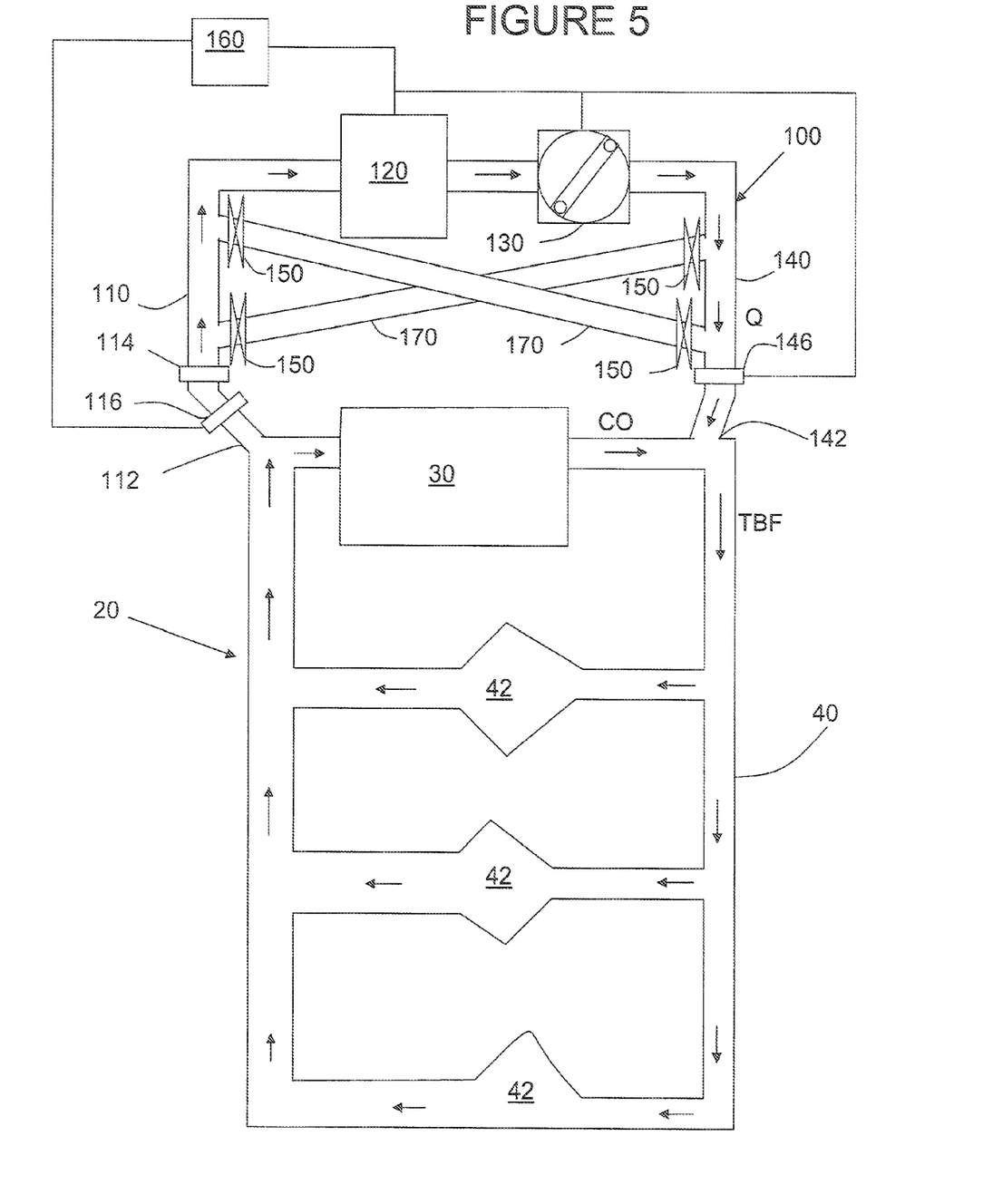
FIG. 5 is a schematic of an extracorporeal circuit with bridge tubing in a forward extracorporeal flow configuration.
Figure 6:
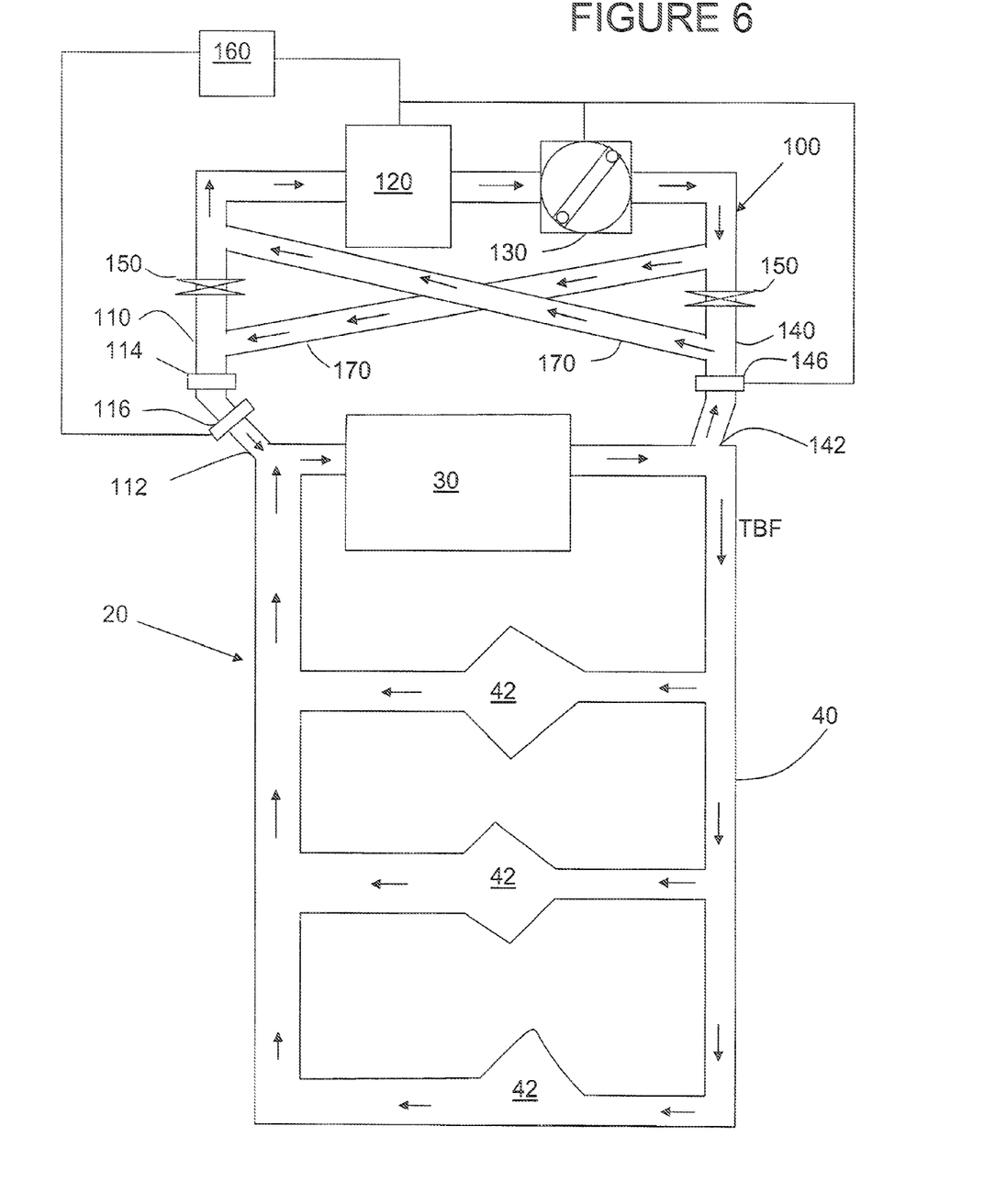
FIG. 6 is a schematic of the extracorporeal circuit of FIG. 5, with selective flow in the bridge tubing to provide a reversed flow of the extracorporeal circuit.

Alternatively, as seen in FIG. 3, the lines between the pump 130 and the circulation system 20 (patient) can be reversed. This line reversal can be achieved by, for example, using a special line reversal device, line switching or with simple re-clamping of tubing in the extracorporeal circuit 100 (an example of the line clamping is seen in FIGS. 5 and 6). An advantage to this configuration of the flow reversal lies in a constant forward flow through the pump 130 and relevant extracorporeal components. Thus, only in the local region of the interface between the extracorporeal circuit 100 and the circulation system 20 (patient) is the flow reversed so that indicator if introduced into the extracorporeal circuit 100 passes into the venous portion of the cardiopulmonary system 30, through the cardiopulmonary system and a portion is withdrawn through the arterial line 140 of the extracorporeal circuit. Again, the dilution curves can be measured anywhere within the extracorporeal circuit 100, but preferably along the arterial line 140.

Figure 4:
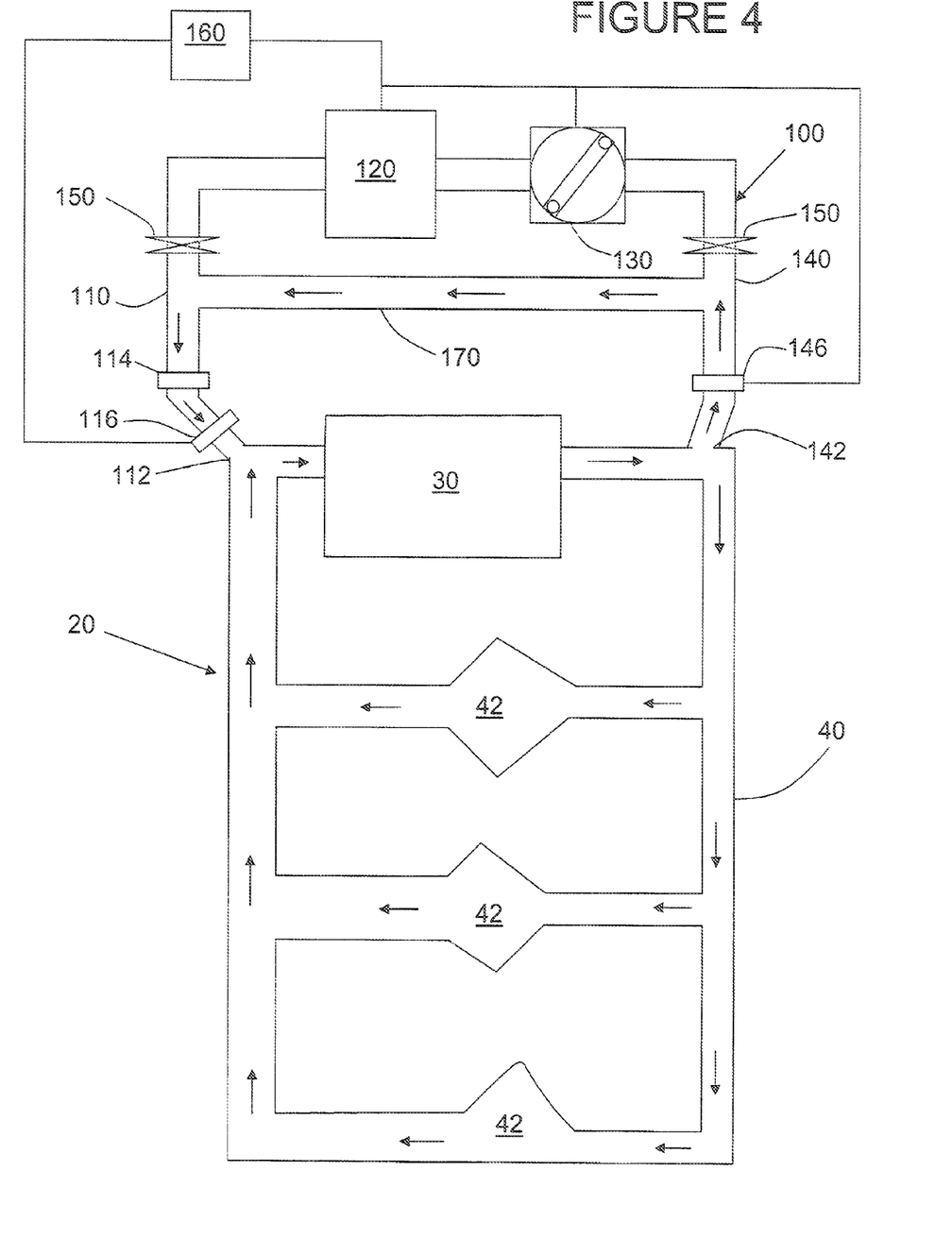
FIG. 4 is a schematic of an extracorporeal circuit with a reversed extracorporeal flow configuration, such as by extracorporeal bridge control.

In the extracorporeal circuit 100 of some cardiopulmonary support systems, such as ECMO, there is a bridge (bypass) tubing 170 between the withdraw and return lines, as seen in FIG. 4). The bridge tubing 170 is usually clamped to preclude flow therethrough. However, the bridge tubing 170 is periodically opened to insure that blood is not clotted. The bridge tubing 170 is established for emergency situations, for example to prevent flow from the ECMO if bubbles or clots appear or there is a need to substitute extracorporeal lines. The bridge tubing 170 can be used to measure the cardiac output CO. Specifically, the pump 130 can be stopped, clamped off by clamps 150 (shown in FIG. 4) or run through a parallel circuit (not shown). When the pump 130 is stopped (clamped or run through the parallel circuit), the blood will flow in the bridge tubing 170 by patient pressure gradient from the artery to vein. This flow can allow performing cardiac output measurements, as seen in FIG. 4. However, this configuration of flow reversal is subject to the limitation that blood flow through the bridge tubing 170 depends on heart performance (and hence pressure from the systemic system) and hydrodynamics resistance (length of the bridge, the diameter of the tubing as well as the size of the cannula). These factors can reduce the stability of the blood flow rate through the bridge tubing 170. It is also understood that an additional pump (not shown) can be included in this configuration to assist in providing an acceptable flow.

Referring to FIG. 5, the extracorporeal circuit 100 can include the bridge tubing 170 to define a flow reversing structure in cooperation with clamps 150. That is, the extracorporeal circuit 100 can be clamped, as seen in FIG. 5, to provide normal, forward flow through the circuit (the pump 130 and oxygenator 120), with no flow through the bridge tubing. Although four clamps 150 are shown it is understood fewer, or more clamps can be used are desired to maintain the forward flow.

Referring to FIG. 6, wherein the clamps are removed (or selectively opened) on the bridge tubing 170 and closed on the shown portions of the venous line and arterial line, flow is diverted through the bridge tubing to effect a reversed flow through the venous cannula 112 and the arterial cannula 142.

For each of the flow reversal configurations, it is understood the reversed flow is selected to reduce or minimize stress to the heart (and cardiopulmonary system 30).

After flow in at least the parts of the venous and the arterial lines 110, 140 of the extracorporeal circuit 100 is reversed, the indicator is introduced so as to pass from the venous portion of the circulation system 20 to pass through the cardiopulmonary system 30 and be withdrawn into the arterial line 140 of the extracorporeal circuit 100 to be measured (recorded) by the sensor 146 in (or associated with) the extracorporeal circuit. The indicator can be introduced via any place of the extracorporeal circuit 100, and preferably the venous line 100 of the extracorporeal circuit, as well as intravenously into the venous portion of the circulation system 20.

In one configuration of the invention, a single dilution indicator sensor 146 is employed in the arterial line. As set forth in the description of the extracorporeal circuit 100, the preferred location of the single sensor 146 is close to the place of arterial cannulation, seen at 142 in FIG. 2, and the preferred location for indicator introduction is near the site of venous cannulation seen at 112 in FIG. 2. In this construction, the indicator will be less dispersed in the lines of extracorporeal circuit 100.

It is also understood that location of dilution sensor 146 in the arterial line 140 is close to the arterial cannula 142 is beneficial as the measured or recorded dilution curves will be less disturbed after leaving cardiopulmonary system 30, than if recorded in the venous line 110 after passing through the pump 130 or other components of extracorporeal system 100.

The resulting dilution curve is measured or recorded by sensor, such as in the extracorporeal system 100.

The cardiac output CO will be given by:

$$CO = \frac{Vi}{S} \quad \text{(Eq. 2)}$$

Where $Vi$ is the volume of the introduced indicator and $S$ is the area of the dilution curve (concentration of indicator) measured in the extracorporeal circuit 100 from the blood (and indicator) flowing from the arterial circulation system (cardiopulmonary circuit 30). The introduction of the indicator can be a relatively quick (short duration) injection, a timed or measured injection, or a continuous injection.

It is understood that different formula can be used to determine the cardiac output, depending upon the specific indicator, the way the indicator is introduced, as is described in literature and textbooks.

It is also contemplated that the indicator can be introduced in the arterial line 140 just upstream of the sensor 146 (in FIGS. 2-4), such that a first dilution curve S1 is measured (recorded) prior to the indicator passing the remainder of the extracorporeal circuit 100 and subsequently entering the cardiopulmonary system 30, then passing into the arterial line to be measured again to provide a second dilution curve S. In this configuration, the cardiac output CO is given by:

$$CO = Q \cdot \left(\frac{S1}{S}\right) \quad \text{(Eq. 3)}$$

If the sensor measures the pump flow Q, or it is known, then the cardiac output CO can be calculated by equation 3, were S1 and S are areas under concentration curves or values that are proportional (related) to such curves. It is understood that different formula can be used to determine the cardiac output, depending upon the specific indicator and the way the indicator is introduced.

In the two sensor configuration, as shown in FIG. 2, (the second sensor 116 being disposed in the venous line 110 downstream of the indicator injection site), for two matched sensors, the cardiac output CO is given by:

$$CO = Q \cdot \left(\frac{S1}{S}\right) \quad \text{(Eq. 3a)}$$

Where S1 is the area under the dilution concentration curve measured before the indicator enters the circulation system 20 by the sensor 116 on the venous line 110, or value related to the dilution concentration.

It is further contemplated that analogous sensor and introduction sites can be employed for the configuration of FIG. 3.

Figure 7:
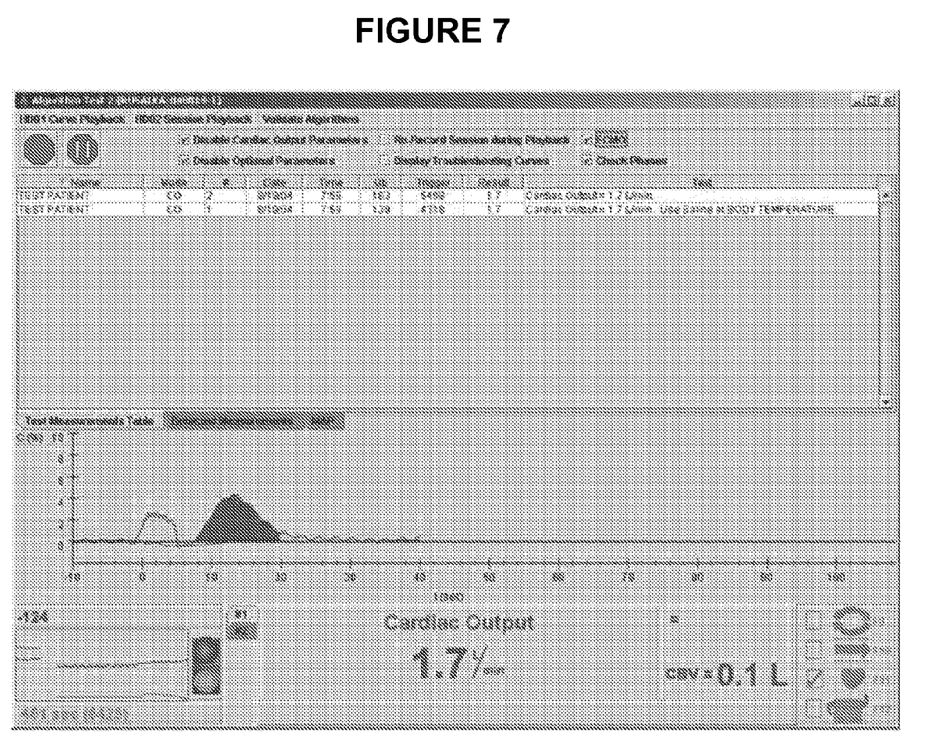
FIG. 7 is a graphical representation of a dilution curve measured at two locations in the extracorporeal circuit.

As a representative example of the configuration of FIG. 2, the sensors are ultrasound dilution sensors, and wherein sensor 116 or 146 also measures blood flow in the extracorporeal circuit, and particularly the venous line. Injection of a 10 ml of saline indicator produces first dilution curve (1) from the sensor 116, seen in FIG. 7, and after the indicator has traveling through the cardiopulmonary system 30, the sensor 146 produces second dilution curve (2). From these measurements, the cardiac output is calculated via Equation 3a. In FIG. 7, the scale of the first curve is different than the scale of the second curve.

While the invention has been described in conjunction with specific embodiments thereof, it is evident that many alternatives, modifications, and variations will be apparent to those skilled in the art in light of the foregoing description. Accordingly, the present invention is intended to embrace all such alternatives, modifications, and variations as fall within the spirit and broad scope of the appended claims.

The invention claimed is:

1. A method of measuring a patient cardiac output in a patient vascular system coupled to an extracorporeal cardiopulmonary support circuit, the method comprising:
   (a) reversing a flow in an extracorporeal arterial line of the extracorporeal cardiopulmonary support circuit to withdraw blood from an arterial portion of the patient vascular system and return the flow through an extracorporeal venous line of the extracorporeal cardiopulmonary support circuit to a venous portion of the patient vascular system;
   (b) measuring an indicator dilution curve in the extracorporeal cardiopulmonary support circuit; and
   (c) determining the patient cardiac output corresponding to the measured indicator dilution curve.

2. The method of claim 1, further comprising introducing an indicator into the patient vascular system.

3. The method of claim 1, further comprising introducing an indicator into the venous portion of the patient vascular system.

4. The method of claim 1, further comprising introducing an indicator into the extracorporeal cardiopulmonary support circuit.

5. The method of claim 1, further comprising introducing an indicator into the extracorporeal arterial line.

6. The method of claim 1, further comprising measuring the indicator dilution curve in the extracorporeal arterial line.

7. The method of claim 1, further comprising prior to reversing the flow in the extracorporeal arterial line, introducing a forward flow in the extracorporeal circuit from the venous portion of the vascular system to the arterial portion of the vascular system.

8. The method of claim 1, further comprising reversing the flow in the extracorporeal arterial line by reversing a connection of an extracorporeal venous line and the extracorporeal arterial line between the extracorporeal cardiopulmonary support circuit and the patient vascular system.

9. The method of claim 1, further comprising reversing the flow in the extracorporeal arterial line by passing blood flow through a bridge tubing in the extracorporeal cardiopulmonary support circuit.

10. The method of claim 1, further comprising introducing an indicator into the patient vascular system by one of changing one of a filtration rate of the blood and a treatment of the blood.

11. The method of claim 1, wherein measuring the indicator dilution curve in the extracorporeal cardiopulmonary support circuit includes sensing one of a temperature, electrical impedance, optical property, density, ultrasound velocity, glucose concentration, physical blood property and chemical blood property.

12. The method of claim 1, further comprising withdrawing blood from a venous portion of the patient vascular system through an extracorporeal venous line of the extracorporeal cardiopulmonary support circuit and delivering blood to the arterial portion of the patient vascular system through the extracorporeal arterial line of the extracorporeal cardiopulmonary support circuit prior to reversing the flow.

13. A method of determining cardiac output, the method comprising:
   (a) passing a dilution indicator from a venous portion of the patient vascular system, through a cardiopulmonary system of the patient vascular system to an arterial portion of the patient vascular system;
   (b) reversing a flow in an arterial line of an extracorporeal cardiopulmonary support circuit to withdraw blood from the arterial portion of the patient vascular system; and
   (c) determining a cardiac output corresponding to the dilution indicator in the extracorporeal cardiopulmonary support circuit.

14. The method of claim 13, further comprising measuring an indicator dilution curve in the arterial line of the extracorporeal cardiopulmonary support circuit.

15. The method of claim 13, further comprising introducing the dilution indicator into the venous portion of the patient vascular system.

16. The method of claim 13, further comprising introducing the dilution indicator into the extracorporeal cardiopulmonary support circuit.

17. The method of claim 13, further comprising introducing an indicator into the patient vascular system by one of changing one of a filtration rate of the blood and a treatment of the blood.

18. The method of claim 13, further comprising measuring the indicator dilution in the extracorporeal cardiopulmonary support circuit by sensing one of a temperature, electrical impedance, optical property, density, ultrasound velocity, glucose concentration, physical blood property and chemical blood property.

19. A method of determining cardiac output, the method comprising:
   (a) reversing a flow in an arterial line of an extracorporeal cardiopulmonary support circuit to withdraw blood from an arterial portion of a patient vascular system into the arterial line of the extracorporeal cardiopulmonary support circuit; and
   (b) determining a cardiac output corresponding to a dilution indicator passing from a cardiopulmonary system to an arterial portion of a patient vascular system and into the arterial line of the extracorporeal cardiopulmonary support circuit.

20. The method of claim 19, wherein reversing the flow in the arterial line of the extracorporeal cardiopulmonary support circuit includes one of employing a line reversal device, line switching and re-clamping of a portion of tubing in the extracorporeal cardiopulmonary support circuit.

* * * * *